United States Patent
Kadow et al.

(10) Patent No.: US 8,324,212 B2
(45) Date of Patent: Dec. 4, 2012

(54) COMPOUNDS FOR THE TREATMENT OF HEPATITIS C

(75) Inventors: John F. Kadow, Wallingford, CT (US); Richard Pracitto, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 10 days.

(21) Appl. No.: 13/031,777

(22) Filed: Feb. 22, 2011

(65) Prior Publication Data

US 2012/0046294 A1 Feb. 23, 2012

Related U.S. Application Data

(60) Provisional application No. 61/308,084, filed on Feb. 25, 2010.

(51) Int. Cl.
*A61K 31/50* (2006.01)
*C07D 487/00* (2006.01)

(52) U.S. Cl. .................... 514/252.05; 544/235; 544/236

(58) Field of Classification Search ................. 544/235, 544/236; 514/252.05
See application file for complete search history.

(56) References Cited

U.S. PATENT DOCUMENTS

| | | | |
|---|---|---|---|
| 7,265,152 B2 | 9/2007 | Saha et al. | |
| 7,868,037 B2 | 1/2011 | Karp et al. | |
| 7,994,171 B2 | 8/2011 | Yeung et al. | |
| 2009/0281336 A1 | 11/2009 | Saha et al. | |
| 2010/0063068 A1 | 3/2010 | Pracitto et al. | |
| 2010/0093694 A1 | 4/2010 | Yeung et al. | |

FOREIGN PATENT DOCUMENTS

| | | |
|---|---|---|
| JP | 57-123181 | 7/1982 |
| WO | WO 02/16359 | 2/2002 |
| WO | WO 02/078701 | 10/2002 |
| WO | WO 2004/041201 | 5/2004 |
| WO | WO 2008/125874 | 10/2008 |
| WO | WO 2009/101022 | 8/2009 |
| WO | WO 2009/137493 | 11/2009 |
| WO | WO 2009/137500 | 11/2009 |
| WO | WO 2011/103063 | 8/2011 |
| WO | WO 2011/16896 | 9/2011 |
| WO | WO 2011/106929 | 9/2011 |
| WO | WO 2011/106992 | 9/2011 |

OTHER PUBLICATIONS

U.S. Appl. No. 13/043,747, filed Mar. 9, 2011, Yeung et al.
U.S. Appl. No. 13/167,356, filed Jun. 23, 2011, Yeung et al.
Database Caplus [Online], Chemical Abstracts Service, Columbus, OH, US, Grinev, A.N. et al., "Aminomethyl and aminomethyl derivatives of 5-methoxybenzofuran", Zhurnal Obshchei Khimii, 33(5):1436-1442, Coden: ZOKHA4; ISSN: 0044-460X (1963), retrieved from STN Database, Accession No. 1963:469003, RN 94004-97-4, 94623-08-2, 95220-34-1, Abstract.
Cheung, M., "The identification of pyrazolo[1,5-*a*]pyridines as potent p38 kinase inhibitors", Bioorganic & Medicinal Chemistry Letters, vol. 18, pp. 5428-5430 (2008).
Elsner, J. et al., "Bicyclic melatonin receptor agonists containing a ring-junction nitrogen: Synthesis, biological evaluation, and molecular modeling of the putative bioactive conformation", Bioorganic & Medicinal Chemistry, vol. 14, pp. 1949-1958 (2006).
Flint, M. et al., "Selection and Characterization of Hepatitis C Virus Replicons Dually Resistant to the Polymerase and Protease Inhibitors HCV-796 and Boceprevir (SCH 503034)", Antimicrobial Agents and Chemotherapy, vol. 53, No. 2, pp. 401-411 (2009).
Hang, J.Q. et al., "Slow Binding Inhibition and Mechanism of Resistance of Non-nucleoside Polymerase Inhibitors of Hepatitis C Virus", The Journal of Biological Chemistry, vol. 284, No. 23, pp. 15517-15529 (2009).
Kakehi, A. et al., "Preparation of New Nitrogen-Bridged Heterocycles. XIV. Further Investigation of the Desulfurization and the Rearrangement of Pyrido[1,2-*d*]-1,3,4-thiadiazine Intermediates", Chem. Pharm. Bull., vol. 35, No. 1, pp. 156-169 (1987).
Miki, Y. et al., "Acid-Catalyzed Reactions of 3-(Hydroxymethyl)- and 3-(1- Hydroxyethyl)pyrazolo[1,5-*a*]pyridines", J. Heterocyclic Chem., vol. 26, pp. 1739-1745 (1989).

*Primary Examiner* — Paul V. Ward
(74) *Attorney, Agent, or Firm* — James Epperson

(57) ABSTRACT

The disclosure provides compounds of formula I, including their salts, as well as compositions and methods of using the compounds. The compounds have activity against hepatitis C virus (HCV) and may be useful in treating those infected with HCV.

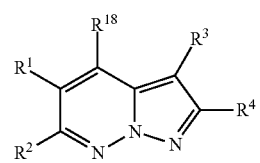

I

14 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/308,084 filed Feb. 25, 2010.

BACKGROUND OF THE INVENTION

The disclosure generally relates to the novel compounds of formula I, including their salts, which have activity against hepatitis C virus (HCV) and are useful in treating those infected with HCV. The disclosure also relates to compositions and methods of using these compounds.

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. Engl. J. Med. 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., Journal of Virology 2002, 3482-3492; and Defrancesco and Rice, Clinics in Liver Disease 2003, 7, 211-242.

Currently, the most effective HCV therapy employs a combination of alpha-interferon and ribavirin, leading to sustained efficacy in 40% of patients (Poynard, T. et al. Lancet 1998, 352, 1426-1432). Recent clinical results demonstrate that pegylated alpha-interferon is superior to unmodified alpha-interferon as monotherapy (Zeuzem, S. et al. N. Engl. J. Med. 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

HCV-796, an HCV NS5B inhibitor, showed an ability to reduce HCV RNA levels in patients. The viral RNA levels decreased transiently and then rebounded during dosing when treatment was with the compound as a single agent but levels dropped more robustly when combined with the standard of care which is a form of interferon and ribavirin. The development of this compound was suspended due to hepatic toxicity observed during extended dosing of the combination regimens. U.S. Pat. No. 7,265,152 and the corresponding PCT patent application WO2004/041201A2 describe compounds of the HCV-796 class.

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I,

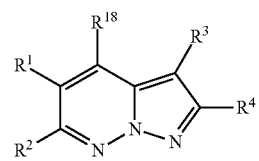

where:
$R^1$ is halo, alkyl, cycloalkyl, alkoxy, dioxothiazinyl, $(R^5)(R^6)N$,

pyridinyl or phenyl, where said pyridinyl or phenyl is substituted with 1-2 substituents selected from the group consisting of alkyl, hydroxyalkyl, alkoxyalkyl, $((R^7)(R^8)N)$alkyl, hydroxy, alkoxy, $(R^7)(R^8)N$, carboxy, alkoxycarbonyl, and $CON(R^{16})(R^{17})$, and where said pyridinyl or phenyl is also substituted with 0-2 halo, alkyl, alkoxy, pyridinyl, phenyl, halophenyl, (halo)$(CON(R^7)(R^8))$phenyl, or (alkoxy)$(CON(R^7)(R^8))$phenyl substituents;

$R^2$ is hydrogen, halo, alkyl, cycloalkyl, alkoxy, or $(R^5)(R^6)N$;
$R^3$ is cyano, alkoxycarbonyl, (cycloalkyl)oxycarbonyl, (alkylsulfonyl)aminocarbonyl, $CON(R^{11})(R^{12})$, $(R^{13})(R^{14})NCONH$, triazolyl, thiazolyl, or tetrazolyl;

R⁴ is phenyl substituted with 0-2 halo, alkoxy, phenoxy, or halophenoxy substituents;

R⁵ is hydrogen, alkyl, cycloalkyl, (cycloalkyl)alkyl, benzyl, alkylcarbonyl, haloalkylcarbonyl, phenylcarbonyl, (alkoxyphenyl)carbonyl, alkylsulfonyl, phenylsulfonyl, (alkoxyphenyl)sulfonyl or (haloalkoxyphenyl)sulfonyl;

R⁶ is hydrogen, alkyl, hydroxyalkyl, or alkoxyalkyl;

or R⁵ and R⁶ taken together with the nitrogen to which they are attached is dioxothiazinyl;

R⁷ is hydrogen or alkyl;

R⁸ is hydrogen or alkyl;

R⁹ is hydrogen or alkyl;

R¹⁰ is hydrogen or alkyl;

or R⁹ and R¹⁰ taken together is ethylene, propylene, butylene, or pentylene, and is substituted with 0-2 flourine atoms;

R¹¹ is hydrogen or alkyl;

R¹² is hydrogen or alkyl;

or R¹¹ and R¹² taken together with the nitrogen to which they are attached is azetidinyl, pyrrolidinyl, piperidinyl, piperazinyl, or morpholinyl;

R¹³ is hydrogen or alkyl;

R¹⁴ is hydrogen or alkyl;

or R¹³ and R¹⁴ taken together with the nitrogen to which they are attached is azetidinyl, pyrrolidinyl, piperidinyl, piperazinyl, or morpholinyl;

R¹⁵ is alkyl or cycloalkyl;

R¹⁶ is hydrogen, alkyl,

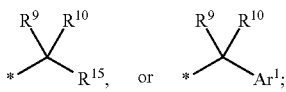

R¹⁷ is hydrogen or alkyl;

R¹⁸ is hydrogen, halo, alkyl or alkoxy; and

Ar¹ is isoxazolyl, oxazolyl, oxadiazolyl, pyrazolyl, pyridinyl, pyrimidinyl, pyridazinyl, pyrazinyl, triazinyl, or phenyl; and is substituted with 0-3 halo, alkyl, haloalkyl, alkoxy, (R⁷)(R⁸)N, or phenyl substituents;

or a pharmaceutically acceptable salt thereof.

Another aspect of the invention is a compound of formula I where:

R¹ is pyridinyl or phenyl and is substituted with 1 substituent selected from the group consisting of carboxy, alkoxycarbonyl, and CON(R¹⁶)(R¹⁷), and is also substituted with 0-2 halo, alkyl, or alkoxy substituents;

R² is hydrogen, halo, alkyl, cycloalkyl, alkoxy, or (R⁵)(R⁶)N;

R³ is CON(R¹¹)(R¹²);

R⁴ is phenyl substituted with 0-2 halo, alkoxy, phenoxy, or halophenoxy substituents;

R⁹ is hydrogen or alkyl;

R¹⁰ is hydrogen or alkyl;

or R⁹ and R¹⁰ taken together is ethylene, propylene, butylene, or pentylene;

R¹¹ is hydrogen or alkyl;

R¹² is hydrogen or alkyl;

or R¹¹ and R¹² taken together with the nitrogen to which they are attached is azetidinyl, pyrrolidinyl, piperidinyl, piperazinyl, or morpholinyl;

R¹⁶ is hydrogen, alkyl, or

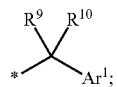

R¹⁷ is hydrogen or alkyl;

R¹⁸ is hydrogen; and

Ar¹ is isoxazolyl, oxazolyl, oxadiazolyl, pyrazolyl, pyridinyl, pyrimidinyl, pyridazinyl, pyrazinyl, triazinyl, or phenyl; and is substituted with 0-3 halo, alkyl, haloalkyl, or alkoxy substituents;

or a pharmaceutically acceptable salt thereof.

Another aspect of the invention is a compound of formula I where:

R¹ is phenyl substituted with 1 CON(R¹⁶)(R¹⁷) substituent and also substituted with 0-2 halo, alkyl, or alkoxy substituents;

R² is hydrogen;

R³ is CON(R¹¹)(R¹²);

R⁴ is phenyl substituted with 0-2 halo, alkoxy, phenoxy, or halophenoxy substituents;

R⁹ is hydrogen or alkyl;

R¹⁰ is hydrogen or alkyl;

or R⁹ and R¹⁰ taken together is ethylene, propylene, butylene, or pentylene;

R¹¹ is hydrogen or alkyl;

R¹² is hydrogen or alkyl;

or R¹¹ and R¹² taken together with the nitrogen to which they are attached is azetidinyl, pyrrolidinyl, piperidinyl, piperazinyl, or morpholinyl;

R¹⁶ is

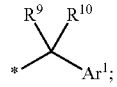

R¹⁷ is hydrogen or alkyl; and

Ar¹ is isoxazolyl, oxazolyl, oxadiazolyl, pyrazolyl, pyridinyl, pyrimidinyl, pyridazinyl, pyrazinyl, triazinyl, or phenyl; and is substituted with 0-3 halo, alkyl, haloalkyl, or alkoxy substituents;

or a pharmaceutically acceptable salt thereof.

Another aspect of the invention is a compound of formula I where R¹ is phenyl substituted with 1 CON(R¹⁶)(R¹⁷) substituent and also substituted with 0-2 halo, alkyl, or alkoxy substituents; R² is hydrogen; R³ is CON(R¹¹)(R¹²); R⁴ is phenyl substituted with 0-2 halo, alkoxy, phenoxy, or halophenoxy substituents; R⁹ and R¹⁰ taken together is ethylene; R¹¹ is alkyl; R¹² is hydrogen; R¹⁶ is

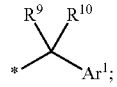

R¹⁷ is hydrogen; and Ar¹ is isoxazolyl, oxazolyl, oxadiazolyl, pyrazolyl, pyridinyl, pyrimidinyl, pyridazinyl, pyrazinyl, triazinyl, or phenyl; or a pharmaceutically acceptable salt thereof.

Another aspect of the invention is a compound of formula I where R¹ is phenyl substituted with 1 CON(R¹⁶)(R¹⁷) substituent and 1 alkyl substituent and 0-1 alkoxy substituents; $R^2$ is hydrogen; $R^3$ is CONHMe; $R^4$ is monofluorophenyl; $R^{16}$ is

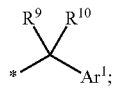

$R^9$ and $R^{10}$ taken together is ethylene; $R^{17}$ is hydrogen; and $Ar^1$ is pyrimidinyl or phenyl; or a pharmaceutically acceptable salt thereof.

Another aspect of the invention is a compound of formula I where $R^1$ is pyridinyl or phenyl and is substituted with 1-2 substituents selected from the group consisting of alkyl, hydroxyalkyl, alkoxyalkyl, $((R^7)(R^8)N)$alkyl, hydroxy, alkoxy, $(R^7)(R^8)N$, carboxy, alkoxycarbonyl, and $CON(R^{16})(R^{17})$, and where said phenyl or pyridinyl is also substituted with 0-2 halo, alkyl, alkoxy, pyridinyl, phenyl, halophenyl, $(halo)(CON(R^7)(R^8))$phenyl, or $(alkoxy)(CON(R^7)(R^8))$phenyl substituents.

Another aspect of the invention is a compound of formula I where $R^1$ is phenyl and is substituted with 1 $CON(R^{16})(R^{17})$ substituent and is also substituted with 0-2 halo, alkyl, alkoxy, pyridinyl, phenyl, halophenyl, $(halo)(CON(R^7)(R^8))$phenyl, or $(alkoxy)(CON(R^7)(R^8))$phenyl substituents.

Another aspect of the invention is a compound of formula I where $R^1$ is phenyl and is substituted with 1 $CON(R^{16})(R^{17})$ substituent and is also substituted with 0-2 halo, alkyl, or alkoxy substituents.

Another aspect of the invention is a compound of formula I where $R^3$ is $CON(R^{11})(R^{12})$.

Another aspect of the invention is a compound of formula I where $R^3$ is $CON(H)(alkyl)$.

Another aspect of the invention is a compound of formula I where $R^4$ is halophenyl.

Another aspect of the invention is a compound of formula I where $R^4$ is phenyl or monofluorophenyl.

Another aspect of the invention is a compound of formula I where $Ar^1$ is phenyl.

Another aspect of the invention is a compound of formula Ia.

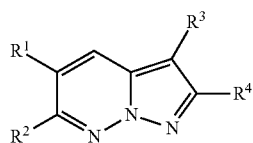

Ia

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, or $Ar^1$ can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R. Substituents which are illustrated by chemical drawing to bond at variable positions on a multiple ring system (for example a bicyclic ring system) are intended to bond to the ring where they are drawn to append. For example, substituents $R^1$ and $R^2$ of formula IV are intended to bond to the benzene ring of formula IV and not to the thiophene ring.

Ethylene means ethanediyl or $-CH_2CH_2-$; propylene means propanediyl or $-CH_2CH_2CH_2-$; butylene means butanediyl or $-CH_2CH_2CH_2CH_2-$; pentylene means pentanediyl or $-CH_2CH_2CH_2CH_2CH_2-$.

Dioxothiazinyl means

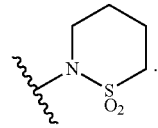

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

The compounds may be made by methods known in the art including those described below. Some reagents and intermediates are known in the art. Other reagents and intermediates can be made by methods known in the art using available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

The compounds may be made by methods known in the art including those described below. Some reagents and intermediates are known in the art. Other reagents and intermediates can be made by methods known in the art using commercially available materials. The variables (e.g. numbered "R" substituents) used to describe the synthesis of the compounds are intended only to illustrate how to make and are not to be confused with variables used in the claims or in other sections of the specification. Abbreviations used within the schemes generally follow conventions used in the art.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

As shown in Scheme 1, some compounds of the invention may be prepared by aminating with an appropriate pyridazine and then cyclizing with a suitably functionized acetylene. Standard removal of protecting groups as described in the experimental section provides the products. Other coupling partners, techniques and conditions are known in the art as are other carbon-carbon bond forming reactions. Acids and esters may be converted to amides by methods known in the art.

Scheme 1.

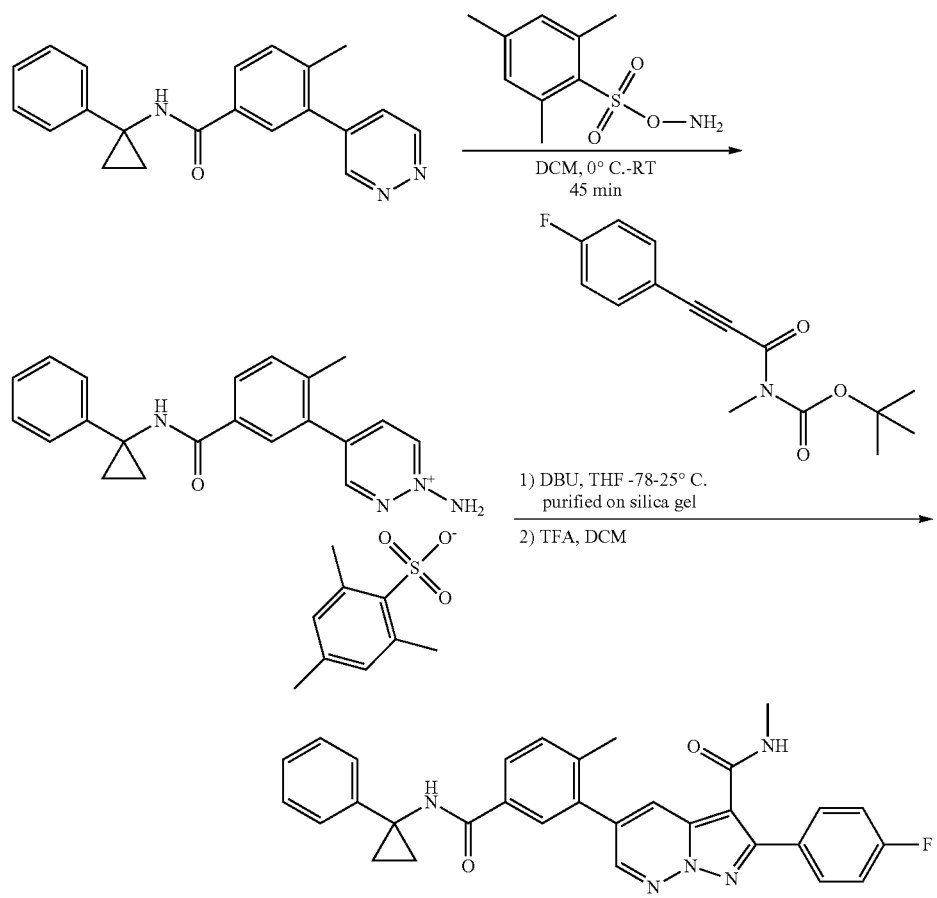

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The E. coli competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCV NS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCV NS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+(C/x)^D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with dH2O, NaCl added to 150 mM final, the FRET peptide diluted to 20 µM final from a 2 mM stock.

To prepare plates, HCV replicon cells, with or without a Renilla luciferase reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity.

The two numbers generated for the compound plate, percent cytoxicity and percent activity were used to determine compounds of interest for further analysis.

HCV Replicon Luciferase Reporter Assay

The HCV replicon luciferase assay was developed to monitor the inhibitory effects of compounds described in the disclosure on HCV viral replication. Utilization of a replicon luciferase reporter assay was first described by Krieger et al (Krieger N, Lohmann V, and Bartenschlager R, *J. Virol.* 75(10):4614-4624 (2001)). HUH-7 cells, constitutively expressing the HCV replicon, were grown in Dulbecco's Modified Eagle Media (DMEM) (Gibco-BRL) containing 10% Fetal calf serum (FCS) (Sigma) and 1 mg/ml G418 (Gibco-BRL). Compounds were serially diluted 3 folds in DMSO for a twenty-point titration and subsequently transferred to sterile 384-well tissue-culture treated plates (Corning cat #3571). The plates were then seeded with 50 µl of cells at a density of $3.0 \times 10^3$ cells/well in DMEM containing 4% FCS (final DMSO concentration at 0.5%). After 3 days incubation at 37° C., cells were analyzed for *Renilla* Luciferase activity using the EnduRen as substrate (Promega cat #E6485). The EnduRen substrate was diluted in DMEM and then added to the plates to a final concentration of 7.5 µM. The plates were incubated for 2 hrs at 37° C. and then read immediately for 30 seconds with Viewlux Imager (PerkinElmer) using a luminescence program. To assess cytotoxicity of compounds, $CC_{50}$ values were generated by multiplexing the EnduRen-containing plates with Cell Titer-Blue (Promega, cat #G8082). 3 µl of Cell-Titer Blue was added to each well and incubated for 8 hrs at 37° C. The fluorescence signal from each well was read, with an excitation wavelength at 525/10 nm and an emission wavelength of 598/10 nm, using the Viewlux Imager.

Representative data for compounds are reported in Table 1.

TABLE 1

| Structure | $IC_{50}$ (µM) | $EC_{50}$ (µM) |
|---|---|---|
| 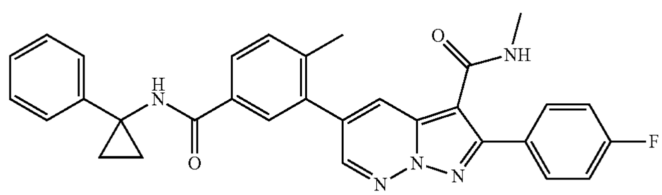 | <0.017 | 0.005 |
| 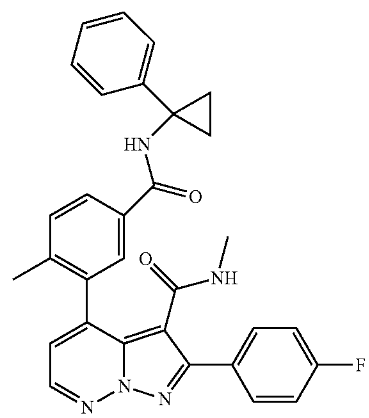 | 3.06 | |
| 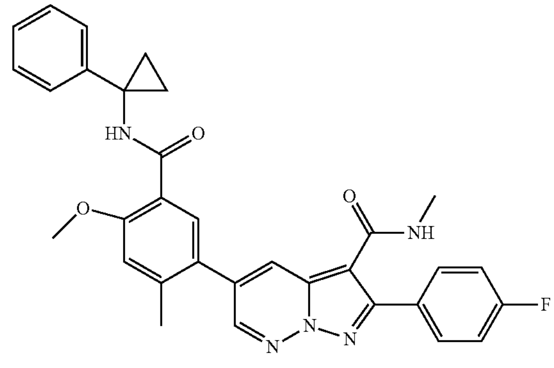 | 0.011 | 0.002 |

TABLE 1-continued

| Structure | IC$_{50}$ (μM) | EC$_{50}$ (μM) |
|---|---|---|
| (structure) | 0.014 | 0.012 |

If no data is entered use the following key: A 0.002 or less to 0.25 μM; B>0.25 μM-<1.0 μM; C 1.0 μM-10.0 μM; D>0.67 μM but an exact value was not determined; E>10.0 μM; F>0.4 μM; but an exact value was not determined; G>1.39 μM but an exact value was not determined; H>0.62 μM but an exact value was not determined; I>4 μM but an exact value was not determined; J>3.7 μM but an exact value was not determined; K>1.23 μM but an exact value was not determined; L>4.17 μM but an exact value was not determined; M>0.5 μM but an exact value was not determined Pharmaceutical Compositions and Methods of Treatment The compounds demonstrate activity against HCV NS5B and can be useful in treating HCV and HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon. Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
| --- | --- | --- |
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |

TABLE 2-continued

| Brand Name | Type of Inhibitor or Target | Source Company |
|---|---|---|
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

DESCRIPTION OF SPECIFIC EMBODIMENTS

Intermediate 1

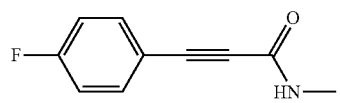

3-(4-fluorophenyl)-N-methylpropiolamide. The preparation of N-methylpropiolamide is described is described in WO1998022429A1, Preparation 2 on page 27 and was used to prepare this intermediate. 3-(4-fluorophenyl)-N-methylpropiolamide could be prepared analogously according to methods for the preparation of 3-(3-fluorophenyl)-N-methylpropiolamide or 3-(2,5-difluorophenyl)-N-methylpropiolamide found in *J. Org. Chem. Vol.* 63, No. 15, 1998, 5050-5058 or for coupling 4-Fluoro iodo benzene to TMS acetylene as found in Organic Letters vol 7, No. 21, 2005, 4753 supplementary info page 1. Thus commercially available 1-Fluoro-4-iodobenzene, N-methylpropiolamide, Pd(PPh$_3$)$_2$Cl$_2$, copper (I) iodide, and triethylamine could be combined and heated to provide the desired product after workup. 1H NMR (400 MHz, CHLOROFORM-d) δ ppm 7.45-7.54 (m, 2 H), 6.99-7.11 (m, 2 H), 6.02 (br. s., 1 H), 2.93 (d, J=5.02 Hz, 3 H). LCMS retention time: 1.405 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 178 (MH$^+$).

Intermediate 2

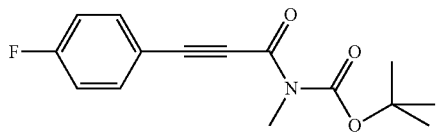

Tert-butyl 3-(4-fluorophenyl)propioloyl(methyl)carbamate. To a solution containing 3-(4-fluorophenyl)-N-methylpropiolamide (10.0 g, 56 mmol), di-tert-butyl dicarbonate (13.5 g, 62 mmol) and THF (282 mL) was added dimethylaminopyridine (0.69 g, 5.6 mmol) in one portion. The solution was maintained for 1 h, concentrated to remove all solvent and purified on silica gel (0-80% ethylacetate/hexanes, 60 min gradient) to afford a white solid. 1H NMR (400 MHz, CHLOROFORM-d) δ ppm 7.59 (dd, J=9.03, 5.27 Hz, 2 H), 7.08 (t, J=8.78 Hz, 2 H), 3.23 (s, 3 H), 1.54-1.61 (m, 9 H). LCMS retention time: 2.397 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 300 (MNa$^+$).

Intermediate 3

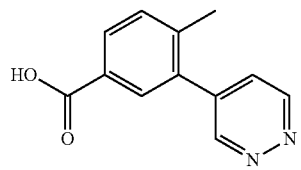

4-methyl-3-(pyridazin-4-yl)benzoic acid. To a degassed mixture containing 4-bromopyridazine (0.10 g, 0.63 mmol), 4-methyl-3-(4,4,5,5-tetramethyl-1,3,2-dioxaborolan-2-yl) benzoic acid (0.18 g, 0.69 mmol), sodium carbonate (0.27 g, 2.52 mmol), dioxane (5.2 mL) and water (1.01 mL) was added tetrakis(tiphenylphosphine)palladium(0) (0.02 g, 0.02 mmol) in one portion under a nitrogen atmosphere. The mixture was heated with fast stirring at 95° C. for 4 h, cooled to room temperature and filtered. The filtered solution was acidified to below pH 4 with 1N HCl (5.0 mL). The resultant precipitate was recovered by filtration, washed with water (3×3.0 mL) and air dried. The resultant tan solid was suspended in n-pentane (4 mL), stirred for 20 min, recovered by filtration and air dried to afford 4-methyl-3-(pyridazin-4-yl) benzoic acid as a tan solid which was used without further purification. LCMS: retention time: 1.325 min. LC data was recorded on a Shimadzu LC-10AS liquid chromatograph equipped with a Sunfire, 5 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 215 ($MH^+$).

Intermediate 4

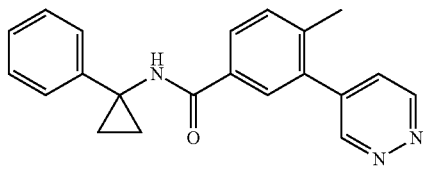

4-methyl-N-(1-phenylcyclopropyl)-3-(pyridazin-4-yl) benzamide. To a solution containing 2-phenylcyclopropan-amine hydrochloride (0.13 g, 0.76 mmol), diisopropylethy-lamine (0.88 mL, 5.0 mmol), 4-methyl-3-(pyridazin-4-yl) benzoic acid (0.14 g, 0.63 mmol) and DMF (4.2 mL) was added HATU (0.48 g, 1.3 mmol) in one portion. The solution was maintained at room temperature for 40 min. and concentrated to a residue. The residue thus obtained was purified on silica gel (0-8% methanol/dichloromethane, 45 min gradient) to afford 4-methyl-N-(1-phenylcyclopropyl)-3-(pyridazin-4-yl)benzamide. 1H NMR (500 MHz, CHLOROFORM-d) δ ppm 9.22-9.28 (m, 1 H), 9.18 (d, J=1.22 Hz, 1 H), 7.75-7.85 (m, 1 H), 7.70 (d, J=1.83 Hz, 1 H), 7.51 (dd, J=5.19, 2.44 Hz, 1 H), 7.37-7.42 (m, 1 H), 7.23-7.33 (m, 5 H), 7.15-7.21 (m, 2 H), 3.70 (dt, J=13.12, 6.56 Hz, 3 H), 3.17 (q, J=7.32 Hz, 3 H), 2.30-2.40 (m, 3 H). LCMS retention time: 1.655 min. LC data was recorded on a Shimadzu LC-10AS liquid chromatograph equipped with a Sunfire C18, 5 micron, C18, 4.6×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% $CH_3CN$/90% $H_2O$/10 mM TFA and solvent B was 10% $H_2O$/90% $CH_3CN$/10 mM TFA. MS data was determined using a Micromass Platform for LC in electrospray mode. m/z 330 ($MH^+$).

Intermediate 5 and Intermediate 6

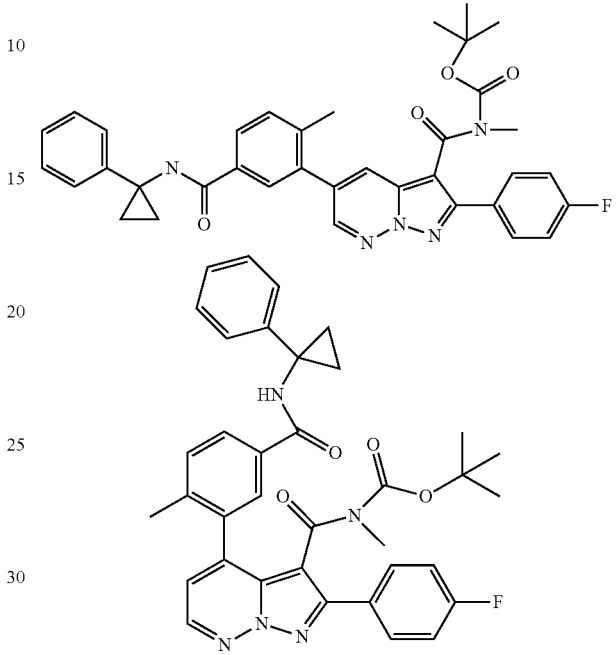

tert-butyl 2-(4-fluorophenyl)-5-(2-methyl-5-(1-phenylcy-clopropylcarbamoyl)phenyl)pyrazolo[1,5-b]pyridazine-3-carbonyl(methyl)carbamate and tert-butyl 2-(4-fluorophe-nyl)-4-(2-methyl-5-(1-phenylcyclopropylcarbamoyl) phenyl)pyrazolo[1,5-b]pyridazine-3-carbonyl(methyl) carbamate. Part A: To a cooled solution (0° C., ice bath) containing 4-methyl-N-(1-phenylcyclopropyl)-3-(pyridazin-4-yl)benzamide (0.21 g, 0.55 mmol) and dichloromethane (4 mL) was added O-(mesitylsulfonyl)hydroxylamine (0.23 g, 0.58 mmol) in dichloromethane (3 mL) quickly, dropwise. The solution was maintained at 0° C. for 5 min, removed from the cooling bath and maintained at ambient temperature for 45 min. The solution was concentrated to a foam and suspended in n-pentane (5 mL) with stirring for 20 min. The solid was collected by filtration and air dried to afford 1-amino-4-(2-methyl-5-(1-phenylcyclopropylcarbamoyl)phenyl)py-ridazin-1-ium 2,4,6-trimethylbenzenesulfonate as a yellow powder (345 $MH^+$). Part B: The product thus obtained in part A was suspended in THF (3.7 mL). tert-butyl 3-(4-fluorophe-nyl)propioloyl(methyl)carbamate (0.19 g, 0.69 mmol) was added and the suspension cooled to −78° C. (dry Ice/acetone bath). DBU (0.17 g, 1.14 mmol) in THF (2 mL) was added dropwise over 5 min. The mixture was left in the cooling bath and allowed to proceed for 20 h at ambient temperature. The mixture was concentrated. Purification on silica gel (30-100% ethyl acetate/hexanes, 60 min gradient) afforded tert-butyl 2-(4-fluorophenyl)-5-(2-methyl-5-(1-phenylcyclo-propylcarbamoyl)phenyl)pyrazolo[1,5-b]pyridazine-3-car-bonyl(methyl)carbamate and tert-butyl 2-(4-fluorophenyl)-4-(2-methyl-5-(1-phenylcyclopropylcarbamoyl)phenyl) pyrazolo[1,5-b]pyridazine-3-carbonyl(methyl)carbamate as separate regioisomers. Tert-butyl 2-(4-fluorophenyl)-5-(2-methyl-5-(1-phenylcyclopropylcarbamoyl)phenyl)pyrazolo

[1,5-b]pyridazine-3-carbonyl(methyl)carbamate: 1H NMR (400 MHz, CHLOROFORM-d) δ ppm 8.35 (d, J=2.26 Hz, 1 H), 8.12 (d, J=2.51 Hz, 1 H), 7.70-7.83 (m, 4 H), 7.42 (d, J=8.03 Hz, 1 H), 7.28-7.37 (m, 5 H), 7.13-7.24 (m, 3 H), 6.91 (s, 1 H), 3.29 (s, 3 H), 2.40 (s, 3 H), 1.40 (d, J=6.27 Hz, 4 H), 1.10 (s, 9 H) LCMS retention time: 2.731 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 620 ($MH^+$). 1H NMR (400 MHz, CHLOROFORM-d) δ ppm 8.68 (d, J=2.51 Hz, 1 H), 8.43 (d, J=2.26 Hz, 1 H), 7.85 (dd, J=7.91, 1.88 Hz, 1 H), 7.72-7.81 (m, 3 H), 7.45 (d, J=8.03 Hz, 1 H), 7.28-7.36 (m, 5 H), 7.16-7.27 (m, 3 H), 5.90 (d, J=4.52 Hz, 1 H), 2.90 (d, J=5.02 Hz, 3 H), 2.43 (s, 3 H), 1.42 (s, 2 H), 1.35-1.41 (m, 2 H).

Tert-butyl 2-(4-fluorophenyl)-4-(2-methyl-5-(1-phenylcyclopropylcarbamoyl)phenyl)pyrazolo[1,5-b]pyridazine-3-carbonyl(methyl)carbamate: 1H NMR (400 MHz, CHLOROFORM-d) δ ppm 8.41 (t, J=5.14 Hz, 1 H), 7.79-7.92 (m, 3 H), 7.46-7.58 (m, 2 H), 7.41 (d, J=8.03 Hz, 1 H), 7.28-7.39 (m, 4 H), 7.10-7.23 (m, 3 H), 6.88-6.97 (m, 1 H), 2.59 (s, 1 H), 2.49 (s, 2 H), 2.39 (s, 1 H), 2.12 (s, 2 H), 1.30-1.43 (m, 4 H), 0.96-1.06 (m, 9 H). LCMS retention time: 2.616 min. LC data was recorded on a Shimadzu LC-10AS liquid chromatograph equipped with a Phenomenex-Luna, 10 micron, C18, 3.0×50 mm column using a SPD-10AV UV-V is detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 620 ($MH^+$).

Example 1

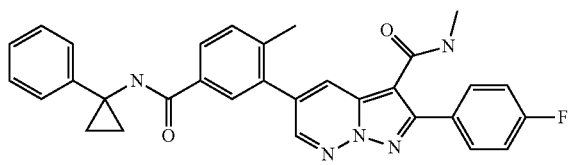

2-(4-fluorophenyl)-N-methyl-5-(2-methyl-5-(1-phenylcyclopropylcarbamoyl)phenyl)pyrazolo[1,5-b]pyridazine-3-carboxamide. To a solution containing tert-butyl 2-(4-fluorophenyl)-5-(2-methyl-5-(1-phenylcyclopropylcarbamoyl)phenyl)pyrazolo[1,5-b]pyridazine-3-carbonyl(methyl)carbamate (0.044 g, 0.065 mmol) and dichloromethane (4 mL) was added TFA (0.41 mL, 5.3 mmol) at room temperature. The solution was maintained for 15 min and concentrated. The resultant residue was purified using preparative HPLC (Waters-Xbridge, 50×100 mm, 5 micron, C18 column; 0.1M ammonium acetate, 0-100% B (B=5% $H_2O$/$CH_3CN$)/A (A=95% $H_2O$/$CH_3CN$), 15 min. gradient) to afford 2-(4-fluorophenyl)-N-methyl-5-(2-methyl-5-(1-phenylcyclopropylcarbamoyl)phenyl)pyrazolo[1,5-b]pyridazine-3-carboxamide as a white solid. Preparative HPLC: retention time: 12.6 min. 1H NMR (400 MHz, CHLOROFORM-d) δ ppm 8.68 (d, J=2.51 Hz, 1 H), 8.43 (d, J=2.26 Hz, 1 H), 7.85 (dd, J=7.91, 1.88 Hz, 1 H), 7.72-7.81 (m, 3 H), 7.45 (d, J=8.03 Hz, 1 H), 7.28-7.36 (m, 5 H), 7.16-7.27 (m, 3 H), 5.90 (d, J=4.52 Hz, 1 H), 2.90 (d, J=5.02 Hz, 3 H), 2.43 (s, 3 H), 1.42 (s, 2 H), 1.35-1.41 (m, 2 H). LCMS retention time: 2.310 min. LC data was recorded on a Shimadzu LC-10AS liquid chromatograph equipped with a Phenomenex-Luna, 10 micron, C18, 3.0×50 mm column using a SPD-10AV UV-V is detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 520 ($MH^+$).

Example 2

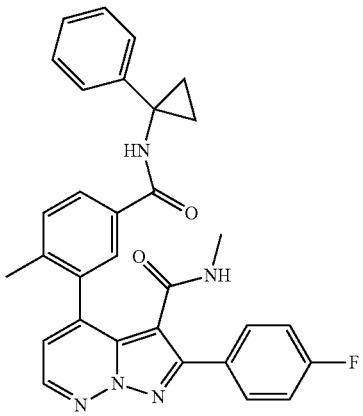

2-(4-fluorophenyl)-N-methyl-4-(2-methyl-5-(1-phenylcyclopropylcarbamoyl)phenyl)pyrazolo[1,5-b]pyridazine-3-carboxamide. To a solution containing tert-butyl 2-(4-fluorophenyl)-4-(2-methyl-5-(1-phenylcyclopropylcarbamoyl)phenyl)pyrazolo[1,5-b]pyridazine-3-carbonylmethyl)carbamate (0.054 g, 0.087 mmol) and dichloromethane (4 mL) was added TFA (0.54 mL, 7.6 mmol) at room temperature. The solution was maintained for 15 min and concentrated. The resultant residue was purified using preparative HPLC (Waters-Xbridge, 50×100 mm, 5 micron, C18 column; 0.1M ammonium acetate, 10-100% B (B=5% $H_2O$/$CH_3CN$)/A (A=95% $H_2O$/$CH_3CN$), 15 min. gradient) to afford 2-(4-fluorophenyl)-N-methyl-4-(2-methyl-5-(1-phenylcyclopropylcarbamoyl)phenyl)pyrazolo[1,5-b]pyridazine-3-carboxamide as a white solid. Preparative HPLC: retention time: 11.8 min. 1H NMR (400 MHz, DMSO-$d_6$) δ ppm 8.92 (s, 1H), 8.63 (d, J=4.52 Hz, 1 H), 7.98 (d, J=4.77 Hz, 1 H), 7.88-7.95 (m, 2 H), 7.85 (dd, J=7.91, 1.63 Hz, 1 H), 7.82 (s, 1 H), 7.47 (d, J=8.28 Hz, 1 H), 7.34 (t, J=8.91 Hz, 2 H), 7.19-7.31 (m, 5 H), 7.11-7.19 (m, 1 H), 2.23 (s, 3 H), 2.08 (d, J=4.52 Hz, 3 H), 1.21-1.34 (m, 4 H). LCMS retention time:

2.188 min. LC data was recorded on a Shimadzu LC-10AS liquid chromatograph equipped with a Phenomenex-Luna, 10 micron, C18, 3.0×50 mm column using a SPD-10AV UV-Vis detector at a detector wave length of 220 nM. The elution conditions employed a flow rate of 4 mL/min, a gradient of 100% solvent A/0% solvent B to 0% solvent A/100% solvent B, a gradient time of 3 min, a hold time of 1 min, and an analysis time of 4 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 520 (MH$^+$).

Intermediate 7

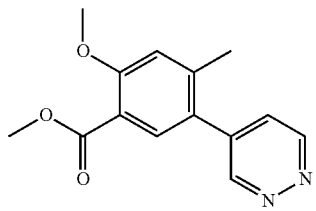

Methyl 2-methoxy-4-methyl-5-(pyridazin-4-yl)benzoate. A mixture containing 4-bromopyridazine hydrobromide (0.20 g, 0.83 mmol), cesium carbonate (1.1 g, 3.3 mmol) and 4-methoxy-5-(methoxycarbonyl)-2-methylphenylboronic acid (0.22 g, 1.0 mmol) was charged with dioxane (8.3 mL). Nitrogen gas was purged through the mixture for 15 min with stirring. Stirring was halted and tris(dibenzylideneacetone)dipalladium(0) (0.38 g, 0.04 mmol) was added, followed by ticyclohexylphosphine (0.04 g, 0.13 mmol) in toluene (0.15 mL). Stirring was resumed and the mixture was heated at 80° C. for 105 minutes under nitrogen gas. The reaction was cooled to RT, filtered and concentrated to a residue. The residue was purified on silica gel (5-100% ethyl acetate/hexanes) to afford methyl 2-methoxy-4-methyl-5-(pyridazin-4-yl)benzoate as an off white solid. $^1$H NMR (400 MHz, CHLOROFORM-d) 9.32-9.14 (m, 2H), 7.75 (s, 1H), 7.46 (dd, J=5.0, 2.3 Hz, 1H), 6.95 (s, 1H), 3.98 (s, 3H), 3.90 (s, 3H), 2.39 (s, 3H). LCMS retention time: 2.805 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 259 (MH$^+$).

Intermediate 8 and Intermediate 9

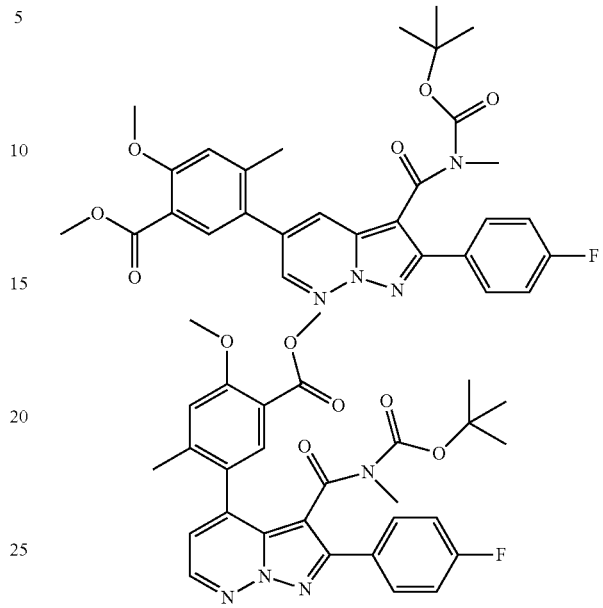

Methyl 5-(3-(tert-butoxycarbonyl(methyl)carbamoyl)-2-(4-fluorophenyl)pyrazolo[1,5-h]pyridazin-5-yl)-2-methoxy-4-methylbenzoate and methyl 5-(3-(tert-butoxycarbonyl(methyl)carbamoyl)-2-(4-fluorophenyl)pyrazolo[1,5-h]pyridazin-4-yl)-2-methoxy-4-methylbenzoate. Part A: To a cooled solution (0° C., ice bath) containing methyl 2-methoxy-4-methyl-5-(pyridazin-4-yl)benzoate (0.16 g, 0.66 mmol) and dichloromethane (3 mL) was added O-(mesitylsulfonyl)hydroxylamine (0.32 g, 0.90 mmol) in dichloromethane (3 mL) quickly, dropwise. The solution was maintained at 0° C. for 5 min, removed from the cooling bath and maintained at ambient temperature for 5 h. The solution was concentrated to afford 1-amino-4-(4-methoxy-5-(methoxycarbonyl)-2-methylphenyl)pyridazin-1-ium 2,4,6-trimethylbenzenesulfonate as a foam (274 MH$^+$). Part B: The product thus obtained in part A was suspended in THF (2.0 mL). tert-butyl 3-(4-fluorophenyl)propioloyl(methyl)carbamate (0.17 g, 0.60 mmol) was added and the suspension cooled to −78° C. (dry Ice/acetone bath). DBU (0.27 g, 1.8 mmol) in THF (1.0 mL) was added dropwise over 2 min. The mixture was left in the cooling bath for 20 min, then removed from cooling and allowed to proceed for 20 h at ambient temperature. The mixture was filtered and concentrated. Purification on silica gel (20-80% ethyl acetate/hexanes, 60 min gradient) afforded methyl 5-(3-(tert-butoxycarbonyl(methyl)carbamoyl)-2-(4-fluorophenyl)pyrazolo[1,5-b]pyridazin-5-yl)-2-methoxy-4-methylbenzoate and methyl 5-(3-(tert-butoxycarbonyl(methyl)carbamoyl)-2-(4-fluorophenyl)pyrazolo[1,5-b]pyridazin-4-yl)-2-methoxy-4-methylbenzoate as separate regioisomers.

5-(3-(tert-butoxycarbonyl(methyl)carbamoyl)-2-(4-fluorophenyl)pyrazolo[1,5-b]pyridazin-5-yl)-2-methoxy-4-methylbenzoate: $^1$H NMR (400 MHz, CHLOROFORM-d) δ 8.35 (d, J=2.3 Hz, 1H), 8.10 (d, J=2.5 Hz, 1H), 7.82-7.73 (m, 3H), 7.17 (t, J=8.7 Hz, 2H), 6.95 (s, 1H), 5.31 (s, 2H), 3.99 (s, 3H), 3.93-3.89 (m, 3H), 3.28 (s, 3H), 2.42 (s, 3H), 1.10 (s, 10H). LCMS retention time: 4.360 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 549 ($MH^+$).

Methyl 5-(3-(tert-butoxycarbonyl(methyl)carbamoyl)-2-(4-fluorophenyl)pyrazolo[1,5-h]pyridazin-4-yl)-2-methoxy-4-methylbenzoate: $^1H$ NMR (400 MHz, CHLOROFORM-d) δ 8.37 (d, J=4.8 Hz, 1H), 7.72 (dd, J=9.0, 5.3 Hz, 2H), 7.66 (s, 1H), 7.11 (t, J=8.8 Hz, 2H), 6.96 (s, 1H), 6.91 (d, J=4.5 Hz, 1H), 3.99 (s, 3H), 3.82 (s, 2H), 2.82 (s, 2H), 2.30-2.26 (m, 3H), 1.04 (s, 9H). LCMS retention time: 4.086 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 549 ($MH^+$).

Intermediate 10

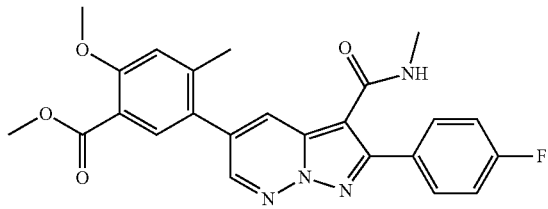

Methyl 5-(2-(4-fluorophenyl)-3-(methylcarbamoyl)pyrazolo[1,5-h]pyridazin-5-yl)-2-methoxy-4-methylbenzoate. To a solution containing methyl 5-(3-(tert-butoxycarbonylmethyl)carbamoyl)-2-(4-fluorophenyl)pyrazolo[1,5-b]pyridazin-5-yl)-2-methoxy-4-methylbenzoate (0.75 g, 0.13 mmol) and dichloromethane (3 mL) was added TFA (0.2 mL, 2.7 mmol) at room temperature. The solution was maintained for 15 min and concentrated to dryness to afford methyl 5-(2-(4-fluorophenyl)-3-(methylcarbamoyl)pyrazolo[1,5-b]pyridazin-5-yl)-2-methoxy-4-methylbenzoate as an off white solid which was used without further purification. $^1H$ NMR (400 MHz, CHLOROFORM-d) δ 8.63 (d, J=2.3 Hz, 1H), 8.45 (d, J=2.3 Hz, 1H), 7.85 (s, 1H), 7.80-7.69 (m, 2H), 7.33-7.25 (m, 2H), 6.98 (s, 1H), 5.97 (br. s., 1H), 3.99 (s, 3H), 3.96-3.85 (m, 3H), 2.92 (d, J=5.0 Hz, 3H), 2.45 (s, 3H). LCMS retention time: 3.758 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 449 ($MH^+$).

Intermediate 11

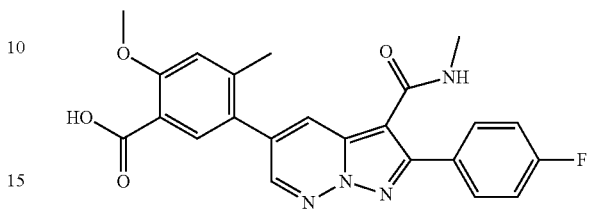

5-(2-(4-fluorophenyl)-3-(methylcarbamoyl)pyrazolo[1,5-b]pyridazin-5-yl)-2-methoxy-4-methylbenzoic acid. To a solution containing methyl 5-(2-(4-fluorophenyl)-3-(methylcarbamoyl)pyrazolo[1,5-b]pyridazin-5-yl)-2-methoxy-4-methylbenzoate (0.061 g, 0.14 mmol) and dioxane (0.7 mL) was added aqueous sodium hydroxide (0.7 mL, 2.0 M). The mixture was stirred at room temperature for 2 h. The solution was adjusted to below pH 4 with aqueous HCl (1.5 mL, 1.0 N). 5-(2-(4-fluorophenyl)-3-(methylcarbamoyl)pyrazolo[1,5-b]pyridazin-5-yl)-2-methoxy-4-methylbenzoic acid precipitated as a tan solid. It was filtered off, washed with water (3×4 mL) and air dried. $^1H$ NMR (400 MHz, CHLOROFORM-d) δ 8.66 (d, J=2.5 Hz, 1H), 8.38 (d, J=2.5 Hz, 1H), 8.16 (s, 1H), 7.83-7.73 (m, 2H), 7.29-7.22 (m, 2H), 7.05 (s, 1H), 5.68 (br. s., 1H), 4.17 (s, 3H), 2.89 (d, J=5.0 Hz, 3H), 2.48 (s, 3H). LCMS retention time: 3.508 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 0.8 mL/min, a gradient of 100% solvent A/0% solvent B to 0% solvent A/100% solvent B, a gradient time of 4 min, a hold time of 1 min, and an analysis time of 5 min where solvent A was 10% methanol/90% $H_2O$/10 mM TFA and solvent B was 10% $H_2O$/90% methanol/10 mM TFA. MS data was determined using a Micromass Platform for LC in electrospray mode. m/z 435 ($MH^+$).

Example 3

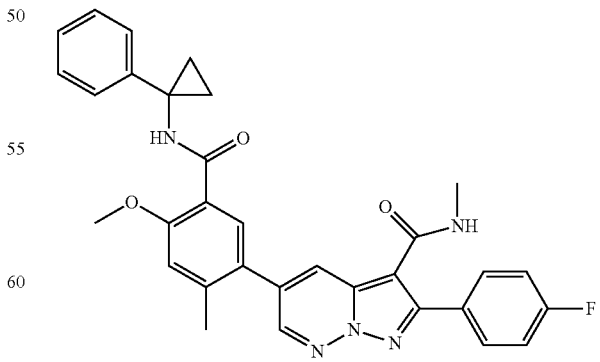

2-(4-fluorophenyl)-5-(4-methoxy-2-methyl-5-(1-phenylcyclopropylcar bamoyl)phenyl)-N-methylpyrazolo[1,5-b]pyridazine-3-carboxamide. To a solution containing 1-phenylcyclopropanamine hydrochloride (0.008 g, 0.05 mmol), diisopropylethylamine (0.05 mL, 0.28 mmol), 5-(2-(4-fluorophenyl)-3-(methylcarbamoyl)pyrazolo[1,5-b]pyridazin-5-yl)-2-methoxy-4-methylbenzoic acid (0.015 g, 0.04 mmol) and DMF (0.23 mL) was added HATU (0.026 g, 0.07 mmol) in one portion. The solution was maintained at room temperature for 1 h. The product was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 15 min. gradient) to afford 2-(4-fluorophenyl)-5-(4-methoxy-2-methyl-5-(1-phenylcyclopropylcarbamoyl)phenyl)-N-methylpyrazolo[1,5-b]pyridazine-3-carboxamide as a white solid. Preparative HPLC retention time: 12.6 min. $^1$H NMR (400 MHz, CHLOROFORM-d) δ 8.61 (d, J=2.5 Hz, 1H), 8.43-8.36 (m, 2H), 8.19 (s, 1H), 7.83-7.72 (m, 2H), 7.35-7.29 (m, 4H), 7.27-7.15 (m, 3H), 6.97 (s, 1H), 5.65 (br. s., 1H), 4.07 (s, 3H), 2.88 (d, J=4.8 Hz, 3H), 2.45 (s, 3H), 1.40 (s, 4H). LCMS retention time: 2.230 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 1.0 mL/min, a gradient of 100% solvent A/0% solvent B to 0% solvent A/100% solvent B, a gradient time of 2 min, a hold time of 1 min, and an analysis time of 3 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 550 (MH$^+$).

Example 4

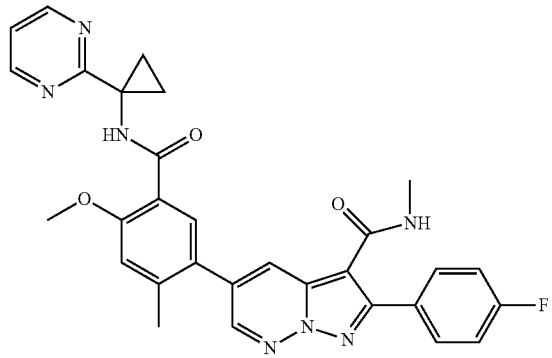

2-(4-fluorophenyl)-5-(4-methoxy-2-methyl-5-(1-(pyrimidin-2-yl)cyclopropylcarbamoyl)phenyl)-N-methylpyrazolo[1,5-b]pyridazine-3-carboxamide. To a solution containing 1-(pyrimidin-2-yl)cyclopropanamine hydrochloride (0.008 g, 0.05 mmol), diisopropylethylamine (0.05 mL, 0.28 mmol), 5-(2-(4-fluorophenyl)-3-(methylcarbamoyl)pyrazolo[1,5-b]pyridazin-5-yl)-2-methoxy-4-methylbenzoic acid (0.015 g, 0.04 mmol) and DMF (0.23 mL) was added HATU (0.026 g, 0.07 mmol) in one portion. The solution was maintained at room temperature for 1 h. The product was purified using preparative HPLC (Waters-Xbridge, 50×100 mm, 5 micron, C18 column; 0.1M ammonium acetate, 0-100% B (B=5% H$_2$O/CH$_3$CN)/A (A=95% H$_2$O/CH$_3$CN), 15 min. gradient) to afford 2-(4-fluorophenyl)-5-(4-methoxy-2-methyl-5-(1-(pyrimidin-2-yl)cyclopropylcarbamoyl)phenyl)-N-methylpyrazolo[1,5-b]pyridazine-3-carboxamide as a white solid. Preparative HPLC retention time: 10.5 min. $^1$H NMR (400 MHz, CHLOROFORM-d) δ 8.72-8.58 (m, 4H), 8.41 (d, J=2.3 Hz, 1H), 8.23 (s, 1H), 7.83-7.74 (m, 2H), 7.26-7.20 (m, 1H), 7.10-7.03 (m, 1H), 6.98 (s, 1H), 5.66 (br. s., 1H), 4.09 (s, 3H), 2.88 (d, J=4.8 Hz, 3H), 2.46 (s, 3H), 1.88-1.81 (m, 2H), 1.59-1.52 (m, 2H). LCMS retention time: 2.057 min. LC data was recorded on a Shimadzu LC-10AS liquid chromatograph equipped with a Phenomenex-Luna, 3 micron, C18, 2.0×50 mm column using a SPD-10AV UV-Vis detector at a detector wave length of 220 nM. The elution conditions employed a flow rate of 1.0 mL/min, a gradient of 100% solvent A/0% solvent B to 0% solvent A/100% solvent B, a gradient time of 2 min, a hold time of 1 min, and an analysis time of 3 min where solvent A was 10% methanol/90% H$_2$O/10 mM TFA and solvent B was 10% H$_2$O/90% methanol/10 mM TFA. MS data was determined using a Micromass Platform for LC in electrospray mode. m/z 552 (MH$^+$).

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. A compound of formula I

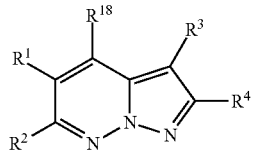

where:
$R^1$ is halo, alkyl, cycloalkyl, alkoxy, dioxothiazinyl, $(R^5)(R^6)N$,

pyridinyl or phenyl, where said pyridinyl or phenyl is substituted with 1-2 substituents selected from the group consisting of alkyl, hydroxyalkyl, alkoxyalkyl, $((R^7)(R^8)N)$alkyl, hydroxy, alkoxy, $(R^7)(R^8)N$, carboxy, alkoxycarbonyl, and $CON(R^{16})(R^{17})$, and where said pyridinyl or phenyl is also substituted with 0-2 halo, alkyl, alkoxy, pyridinyl, phenyl, halophenyl, (halo)$(CON(R^7)(R^8))$phenyl, or (alkoxy)$(CON(R^7)(R^8))$phenyl substituents;

$R^2$ is hydrogen, halo, alkyl, cycloalkyl, alkoxy, or $(R^5)(R^6)N$;

$R^3$ is cyano, alkoxycarbonyl, (cycloalkyl)oxycarbonyl, (alkylsulfonyl)aminocarbonyl, $CON(R^{11})(R^{12})$, $(R^{13})(R^{14})NCONH$, triazolyl, thiazolyl, or tetrazolyl;

$R^4$ is phenyl substituted with 0-2 halo, alkoxy, phenoxy, or halophenoxy substituents;

$R^5$ is hydrogen, alkyl, cycloalkyl, (cycloalkyl)alkyl, benzyl, alkylcarbonyl, haloalkylcarbonyl, phenylcarbonyl, (alkoxyphenyl)carbonyl, alkylsulfonyl, phenylsulfonyl, (alkoxyphenyl)sulfonyl or (haloalkoxyphenyl)sulfonyl;

$R^6$ is hydrogen, alkyl, hydroxyalkyl, or alkoxyalkyl;

or $R^5$ and $R^6$ taken together with the nitrogen to which they are attached is dioxothiazinyl;
$R^7$ is hydrogen or alkyl;
$R^8$ is hydrogen or alkyl;
$R^9$ is hydrogen or alkyl;
$R^{10}$ is hydrogen or alkyl;
or $R^9$ and $R^{10}$ taken together is ethylene, propylene, butylene, or pentylene, and is substituted with 0-2 flourine atoms;
$R^{11}$ is hydrogen or alkyl;
$R^{12}$ is hydrogen or alkyl;
or $R^{11}$ and $R^{12}$ taken together with the nitrogen to which they are attached is azetidinyl, pyrrolidinyl, piperidinyl, piperazinyl, or morpholinyl;
$R^{13}$ is hydrogen or alkyl;
$R^{14}$ is hydrogen or alkyl;
or $R^{13}$ and $R^{14}$ taken together with the nitrogen to which they are attached is azetidinyl, pyrrolidinyl, piperidinyl, piperazinyl, or morpholinyl;
$R^{15}$ is alkyl or cycloalkyl;
$R^{16}$ is hydrogen, alkyl,

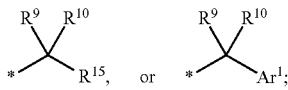

$R^{17}$ is hydrogen or alkyl;
$R^{18}$ is hydrogen, halo, alkyl or alkoxy; and
$Ar^1$ is isoxazolyl, oxazolyl, oxadiazolyl, pyrazolyl, pyridinyl, pyrimidinyl, pyridazinyl, pyrazinyl, triazinyl, or phenyl; and is substituted with 0-3 halo, alkyl, haloalkyl, alkoxy, $(R^7)(R^8)N$, or phenyl substituents;
or a pharmaceutically acceptable salt thereof.

2. A compound of claim 1 where:
$R^1$ is pyridinyl or phenyl and is substituted with 1 substituent selected from the group consisting of carboxy, alkoxycarbonyl, and $CON(R^{16})(R^{17})$, and is also substituted with 0-2 halo, alkyl, or alkoxy substituents;
$R^2$ is hydrogen, halo, alkyl, cycloalkyl, alkoxy, or $(R^5)(R^6)N$;
$R^3$ is $CON(R^{11})(R^{12})$;
$R^4$ is phenyl substituted with 0-2 halo, alkoxy, phenoxy, or halophenoxy substituents;
$R^9$ is hydrogen or alkyl;
$R^{10}$ is hydrogen or alkyl;
or $R^9$ and $R^{10}$ taken together is ethylene, propylene, butylene, or pentylene;
$R^{11}$ is hydrogen or alkyl;
$R^{12}$ is hydrogen or alkyl;
or $R^{11}$ and $R^{12}$ taken together with the nitrogen to which they are attached is azetidinyl, pyrrolidinyl, piperidinyl, piperazinyl, or morpholinyl;
$R^{16}$ is hydrogen, alkyl, or

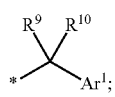

$R^{17}$ is hydrogen or alkyl;
$R^{18}$ is hydrogen; and
$Ar^1$ is isoxazolyl, oxazolyl, oxadiazolyl, pyrazolyl, pyridinyl, pyrimidinyl, pyridazinyl, pyrazinyl, triazinyl, or phenyl; and is substituted with 0-3 halo, alkyl, haloalkyl, or alkoxy substituents;
or a pharmaceutically acceptable salt thereof.

3. A compound of claim 2 where:
$R^1$ is phenyl substituted with 1 $CON(R^{16})(R^{17})$ substituent and also substituted with 0-2 halo, alkyl, or alkoxy substituents;
$R^2$ is hydrogen;
$R^3$ is $CON(R^{11})(R^{12})$;
$R^4$ is phenyl substituted with 0-2 halo, alkoxy, phenoxy, or halophenoxy substituents;
$R^9$ is hydrogen or alkyl;
$R^{10}$ is hydrogen or alkyl;
or $R^9$ and $R^{10}$ taken together is ethylene, propylene, butylene, or pentylene;
$R^{11}$ is hydrogen or alkyl;
$R^{12}$ is hydrogen or alkyl;
or $R^{11}$ and $R^{12}$ taken together with the nitrogen to which they are attached is azetidinyl, pyrrolidinyl, piperidinyl, piperazinyl, or morpholinyl;
$R^{16}$ is

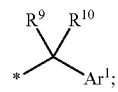

$R^{17}$ is hydrogen or alkyl; and
$Ar^1$ is isoxazolyl, oxazolyl, oxadiazolyl, pyrazolyl, pyridinyl, pyrimidinyl, pyridazinyl, pyrazinyl, triazinyl, or phenyl; and is substituted with 0-3 halo, alkyl, haloalkyl, or alkoxy substituents;
or a pharmaceutically acceptable salt thereof.

4. A compound of claim 3 where $R^1$ is phenyl substituted with 1 $CON(R^{16})(R^{17})$ substituent and also substituted with 0-2 halo, alkyl, or alkoxy substituents; $R^2$ is hydrogen; $R^3$ is $CON(R^{11})(R^{12})$; $R^4$ is phenyl substituted with 0-2 halo, alkoxy, phenoxy, or halophenoxy substituents; $R^9$ and $R^{10}$ taken together is ethylene; $R^{11}$ is alkyl; $R^{12}$ is hydrogen; $R^{16}$ is

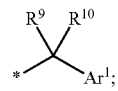

$R^{17}$ is hydrogen; and $Ar^1$ isoxazolyl, oxazolyl, oxadiazolyl, pyrazolyl, pyridinyl, pyrimidinyl, pyridazinyl, pyrazinyl, triazinyl, or phenyl; or a pharmaceutically acceptable salt thereof.

5. A compound of claim 4 where $R^1$ is phenyl substituted with 1 $CON(R^{16})(R^{17})$ substituent and 1 alkyl substituent and 0-1 alkoxy substituents; $R^2$ is hydrogen; $R^3$ is CONHMe; $R^4$ is monofluorophenyl; $R^{16}$ is

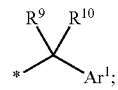

$R^9$ and $R^{10}$ taken together is ethylene; $R^{17}$ is hydrogen; and $Ar^1$ is pyrimidinyl or phenyl; or a pharmaceutically acceptable salt thereof.

6. A compound of claim 1 where $R^1$ is pyridinyl or phenyl and is substituted with 1-2 substituents selected from the group consisting of alkyl, hydroxyalkyl, alkoxyalkyl, $((R^7)(R^8)N)$alkyl, hydroxy, alkoxy, $(R^7)(R^8)N$, carboxy, alkoxycarbonyl, and CON($R^{16}$)($R^{17}$), and where said phenyl or pyridinyl is also substituted with 0-2 halo, alkyl, alkoxy, pyridinyl, phenyl, halophenyl, (halo)(CON($R^7$)($R^8$))phenyl, or (alkoxy)(CON($R^7$)($R^8$))phenyl substituents.

7. A compound of claim 1 where $R^1$ is phenyl and is substituted with 1 CON($R^{16}$)($R^{17}$) substituent and is also substituted with 0-2 halo, alkyl, alkoxy, pyridinyl, phenyl, halophenyl, (halo)(CON($R^7$)($R^8$))phenyl, or (alkoxy)(CON($R^7$)($R^8$))phenyl substituents.

8. A compound of claim 1 where $R^1$ is phenyl and is substituted with 1 CON($R^{16}$)($R^{17}$) substituent and is also substituted with 0-2 halo, alkyl, or alkoxy substituents.

9. A compound of claim 1 where $R^3$ is CON(H)(alkyl).

10. A compound of claim 1 where $R^4$ is halophenyl.

11. A compound of claim 1 where $R^4$ is phenyl or monofluorophenyl.

12. A compound of claim 1 selected from the group consisting of 2-(4-fluorophenyl)-N-methyl-5-(2-methyl-5-(1-phenyl-cyclopropylcarbamoyl)phenyl)pyrazolo[1,5-b]pyridazine-3-carboxamide;

2-(4-fluorophenyl)-5-(4-methoxy-2-methyl-5-(1-phenyl-cyclopropylcarbamoyl)phenyl)-N-methylpyrazolo [1,5-b]pyridazine-3-carboxamide; and 2-(4-fluorophenyl)-5-(4-methoxy-2-methyl-5-(1-(pyrimidin-2-yl)cyclopropylcarbamoyl)phenyl)-N-methylpyrazolo [1,5-b]pyridazine-3-carboxamide;

or a pharmaceutically acceptable salt thereof.

13. A composition comprising a compound of claim 1, or a pharmaceutically acceptable salt thereof, and a pharmaceutically acceptable carrier.

14. A method of treating hepatitis C infection comprising administering a therapeutically effective amount of a compound of claim 1 to a patient.

* * * * *

UNITED STATES PATENT AND TRADEMARK OFFICE
CERTIFICATE OF CORRECTION

PATENT NO. : 8,324,212 B2  
APPLICATION NO. : 13/031777  
DATED : December 4, 2012  
INVENTOR(S) : John F. Kadow et al.

Page 1 of 1

It is certified that error appears in the above-identified patent and that said Letters Patent is hereby corrected as shown below:

On the Title Page:

Item (56), References Cited, under FOREIGN PATENT DOCUMENTS:
    Column 1, change "WO 2011/16896" to -- WO 2011/106896 --.

In the Claims:

Claim 1:
    Column 29, line 8, change "flourine" to -- fluorine --.

Claim 4:
    Column 30, line 47, change "$Ar^1$ isoxazolyl," to -- $Ar^1$ is isoxazolyl, --.

Claim 12:
    Column 32, lines 5 and 6, change "N-methylpyrazolo [1,5-b]" to -- N-methylpyrazolo[ 1,5-b] --.
    Column 32, lines 8 and 9, change "N-methylpyrazolo [1,5-b]" to -- N-methylpyrazolo[1,5-b] --.

Signed and Sealed this  
Sixth Day of May, 2014

Michelle K. Lee  
*Deputy Director of the United States Patent and Trademark Office*